US011494550B2

(12) United States Patent
Higinbotham

(10) Patent No.: US 11,494,550 B2
(45) Date of Patent: *Nov. 8, 2022

(54) METHOD AND APPARATUS FOR INTERACTING WITH MEDICAL WORKSHEETS IN A POINT-OF-CARE BROWSER

(71) Applicant: FUJIFILM SONOSITE, INC., Bothell, WA (US)

(72) Inventor: John D. Higinbotham, Seattle, WA (US)

(73) Assignee: FUJIFILM SONOSITE, INC., Bothell, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/303,551

(22) Filed: Jun. 2, 2021

(65) Prior Publication Data

US 2021/0294968 A1 Sep. 23, 2021

Related U.S. Application Data

(63) Continuation of application No. 16/144,795, filed on Sep. 27, 2018, now Pat. No. 11,042,696.

(Continued)

(51) Int. Cl.
*G06F 16/95* (2019.01)
*G06F 40/174* (2020.01)
(Continued)

(52) U.S. Cl.
CPC .......... *G06F 40/174* (2020.01); *G06F 16/955* (2019.01); *G06F 16/972* (2019.01); *G06F 40/186* (2020.01); *G16H 30/20* (2018.01)

(58) Field of Classification Search
None
See application file for complete search history.

(56) References Cited

U.S. PATENT DOCUMENTS 8,131,569 B2 * 3/2012 Maresh ............... G06Q 30/018
705/3
8,195,483 B2 * 6/2012 Maresh ............... G16H 40/67
705/3

(Continued)

FOREIGN PATENT DOCUMENTS

EP 1528455 5/2005
JP 2002024383 1/2002

(Continued)

OTHER PUBLICATIONS

International Preliminary Report on Patentability for Application No. PCT/US2018/053187 dated May 7, 2020, 8 pages.

(Continued)

*Primary Examiner* — Maikhanh Nguyen
(74) *Attorney, Agent, or Firm* — Womble Bond Dickinson (US) LLP

(57) ABSTRACT

An ultrasound point-of-care system receives a worksheet from a worksheet server. The worksheet is encoded as HTML that is configured to be rendered by a browser component of system software. One or more predefined JavaScript functions in the HTML provide information that is entered by a user into the worksheet and meta-data about the worksheet. System software on the medical device uses an intermediate component or code insertion to execute the JavaScript functions to retrieve the entered information and the meta-data. The system software stores the information locally and packages the retrieved information and meta-data as a DICOM file for transmission to the worksheet server when a computer communication connection to the worksheet server becomes available.

18 Claims, 7 Drawing Sheets

Related U.S. Application Data

(60) Provisional application No. 62/578,277, filed on Oct. 27, 2017.

(51) Int. Cl.
*G16H 30/20* (2018.01)
*G06F 16/955* (2019.01)
*G06F 16/958* (2019.01)
*G06F 40/186* (2020.01)

(56) References Cited

U.S. PATENT DOCUMENTS

| | | | |
|---|---|---|---|
| 8,386,278 B2* | 2/2013 | Maresh | G16H 40/67 705/3 |
| 8,553,965 B2 | 10/2013 | Zhao | |
| 9,805,161 B2 | 10/2017 | Hoshino | |
| 2005/0031181 A1* | 2/2005 | Bi | G16H 50/20 382/132 |
| 2006/0206822 A1 | 9/2006 | DeWitt | |
| 2009/0132285 A1* | 5/2009 | Jakobovits | G06F 3/0482 726/17 |
| 2009/0171679 A1 | 7/2009 | Salgado et al. | |
| 2009/0208076 A1 | 8/2009 | Nakajima et al. | |
| 2009/0210631 A1 | 8/2009 | Bosworth et al. | |
| 2011/0238448 A1* | 9/2011 | Maresh | G16H 30/20 705/3 |
| 2012/0084350 A1 | 4/2012 | Xie | |
| 2012/0197664 A1* | 8/2012 | Maresh | G16H 40/67 705/3 |
| 2012/0278093 A1* | 11/2012 | Amundson | G16H 10/20 705/2 |
| 2013/0208966 A1 | 8/2013 | Zhao et al. | |
| 2014/0114672 A1* | 4/2014 | Wright | G16H 30/20 705/2 |
| 2014/0142984 A1* | 5/2014 | Wright | G06F 21/6245 705/3 |
| 2014/0195602 A1 | 7/2014 | Carricarte et al. | |
| 2016/0147944 A1 | 5/2016 | Douglass | |
| 2017/0024516 A1 | 1/2017 | Okabe et al. | |
| 2018/0218119 A1 | 8/2018 | Ueda et al. | |

FOREIGN PATENT DOCUMENTS

| | | |
|---|---|---|
| JP | 2002024383 A | 1/2002 |
| JP | 2006230636 | 9/2006 |
| JP | 2006230636 A | 9/2006 |
| JP | 2009189541 A | 8/2009 |
| JP | 2011067549 A | 4/2011 |
| WO | 2014085918 A1 | 6/2014 |

OTHER PUBLICATIONS

International Search Report for PCT/US2018/053187 dated Feb. 1, 2019, 3 pages.
PCT Written Opinion of the International Searching Authority for PCT/US2018/053187 dated Feb. 1, 2019, 6 pages.
Extended European Search Report on the Patentability of Application No. 18870763.2-1213/37071536 dated Jul. 15, 2021, 13 pages.
Japanese Office Action and Search Report on the Patentability of Application No. 2020-523272 dated Jun. 8, 2022, 6 pages.
Japanese Office Action and Search Report on the Patentability of Application No. 2020-523272 dated Jun. 8, 2022, 4 pages.

* cited by examiner

METHOD AND APPARATUS FOR INTERACTING WITH MEDICAL WORKSHEETS IN A POINT-OF-CARE BROWSER

CROSS-REFERENCE TO RELATED APPLICATIONS

This application is a continuation of U.S. application Ser. No. 16/144,795 filed Sep. 27, 2018 that was issued as U.S. Pat. No. 11,042,696, which claims the benefit of U.S. Provisional Patent Application No. 62/578,277, filed Oct. 27, 2017, and titled "METHOD AND APPARATUS FOR INTERACTING WITH HTML MEDICAL WORKSHEETS RENDERED IN A BROWSER," which is herein incorporated by reference in its entirety.

TECHNICAL FIELD

The disclosed technology relates to point-of-care medical systems and in particular to systems completing patient care worksheets on a point-of-care ultrasound system without a live server connection.

BACKGROUND

During or at the termination of most medical procedures, a physician or technician is asked to complete a form or worksheet that documents the examinations performed. Such worksheets can store basic information such as the patient's name, doctor's name, procedure type or imaging modality, date and location, etc. In addition, the electronic worksheet can also include still or video images taken during the examination, measurements or annotations, physician notes, diagnosis, etc. The completed worksheets are stored in a Digital Imaging and Communications in Medicine (DICOM) archive server. In addition, some of the information in a completed worksheet can be used by a medical billing system to request compensation for the procedures.

Physicians or technicians can use point-of-care medical systems to complete the worksheets. Point-of-care medical systems can be integrated with medical equipment, such as an ultrasound device, can be operatively connected to such medical equipment either directly or via a network, or can be another computing system (e.g. a computer or tablet) which can execute the system software and receive worksheet input from a user. Existing point-of-care medical systems often come with a set of default, hard-coded worksheets. These can be excessively long or cumbersome for many situations, which results in physicians being less likely to use them. In some cases, the worksheets can be customizable by a clinic or a practice group to reflect a desired workflow for a particular procedure. Worksheet server systems can facilitate the use and customization of a worksheet and allow worksheets to be downloaded to a remote computer or medical device, such as a point-of-care system. In addition, the worksheet server or other systems can receive data entered in a completed worksheet and other DICOM data, can store worksheet data and still or video images (e.g. in a picture archiving and communication system (PACS)), and can interact with billing systems. One such worksheet server system is the QPath E™ server system available from Telexy Healthcare, Inc. of Maple Ridge, BC Canada.

In prior technologies, point-of-care systems are required to have live network server connections to download and view worksheets and allow data entered into worksheets to be signed-off (approved for the next stage in the data review workflow) for transmission to servers. If the connection is lost, when point-of-care devices are used in the field or in locations where an internet or other computer communication connections are unavailable or are unreliable, the worksheet cannot be viewed or completed until the connection is reestablished.

SUMMARY

The inventor has recognized a need for technology that allows a user of a point-of-care system, such as an ultrasound point-of-care system, to interact with and complete worksheets without a live connection to a worksheet server. The disclosed technology addresses this need with point-of-care systems that include system software to interface with a browser component. Interfacing between the system software and browser component allows the system software to obtain worksheet data from the browser component and store it in local storage. This interfacing also allows the system software to retrieve stored worksheet data from the local storage and can cause the worksheet data to be auto-filled into a worksheet in the browser component. When an internet or other computer communication connection becomes available, the point-of-care imaging system transmits worksheet data to the server. As used herein, a "live" connection refers to the ability to communicate between two or more devices. For example, when a point-of-care imaging system is able to send a DICOM package to a server, e.g. via the internet, it has a live connection to that server. However, if the point-of-care imaging system attempted to contact the server but was unable to do so, it would not have a live connection to the server.

In some implementations, a point-of-care system can include system software that includes a browser component. The system software can include the browser component as an integrated element in its display, maintaining the look and feel of the system software. The browser component can render worksheets previously stored in local storage of the point-of-care imaging system or can obtain them dynamically from a worksheet server.

When a user opens a worksheet, via the browser component, the point-of-care imaging system software can determine whether there is data associated with this worksheet stored in the point-of-care imaging system's local memory. If so, the system software of the point-of-care imaging system can obtain the local data and interface with the browser component to auto-fill fields in the worksheet. The user can then interact with the worksheet, whether or not it has auto-filled data.

When a triggering event to save worksheet data occurs, such as when the user performs an action that navigates away from the current Document Object Model (DOM), the system software of the point-of-care system can again interface with the browser component to obtain worksheet data entered in the worksheet fields. Data from the worksheet can be stored in local memory. If the worksheet has been completed (e.g. if it has been signed), the worksheet data can be incorporated into a DICOM package by entering data from the worksheet and other associated data into "tags" in the DICOM package. DICOM tags can be standardized fields defined for particular types of data. In some implementations, a DICOM package can include a "private" tag, which can have various data structures useable by different organizations for different purposes. While data transfers described herein are described as using DICOM packages, other data encapsulations are contemplated, such as JSON blobs or XML blocks. When the DICOM package is complete, e.g. adding images, reports, other worksheet data, etc., the DICOM package can be added to a queue that will transmit the DICOM package to a server when a live network connection is available.

In some implementations, interfacing between the system software element and the browser component element includes employing an intermediary component that interacts with both software elements. A worksheet provided in the browser component can use predefined functions (e.g. JavaScript functions) that provide information about the worksheet. The system software running on the point-of-care imaging device can be configured with identifications of these predefined functions, such as their name, the arguments passed to the functions, and the types of results to be returned. The system software can use the intermediary component to get a reference to one or more of the predefined functions for an intended action, such as getting worksheet data or auto-filling a worksheet with specified fields. The intermediary component can use these references to execute the predefined functions within the browser component and obtain a result, if any. The result can be reformatted for use by the system software. When retrieving information from the worksheet, the system software can package the function results into one or more private DICOM tags, or into other DICOM package fields.

In some embodiments, the intermediary component is a component object model (COM). The COM can include an IDispatch function for obtaining pointer references in the DOM of the browser component, given a function's name, parameter, and result data. The COM can also include an IInvoke function for using the pointers to execute the corresponding functions and obtain results.

In some implementations, interfacing between the system software and the browser component can include injecting code into the scripting interpreter of the browser component. For example, injecting the code can include passing the codes through an API of the browser component. The browser can execute the injected code, e.g. to auto-fill worksheet values or obtain entered worksheet values. The procedure for injecting the code can provide a handle to the result. For example, the handle can be a return value from an API function call or can be a specified memory location, accessible by the system software, to which the result will be written.

DETAILED DESCRIPTION

Figure 1:
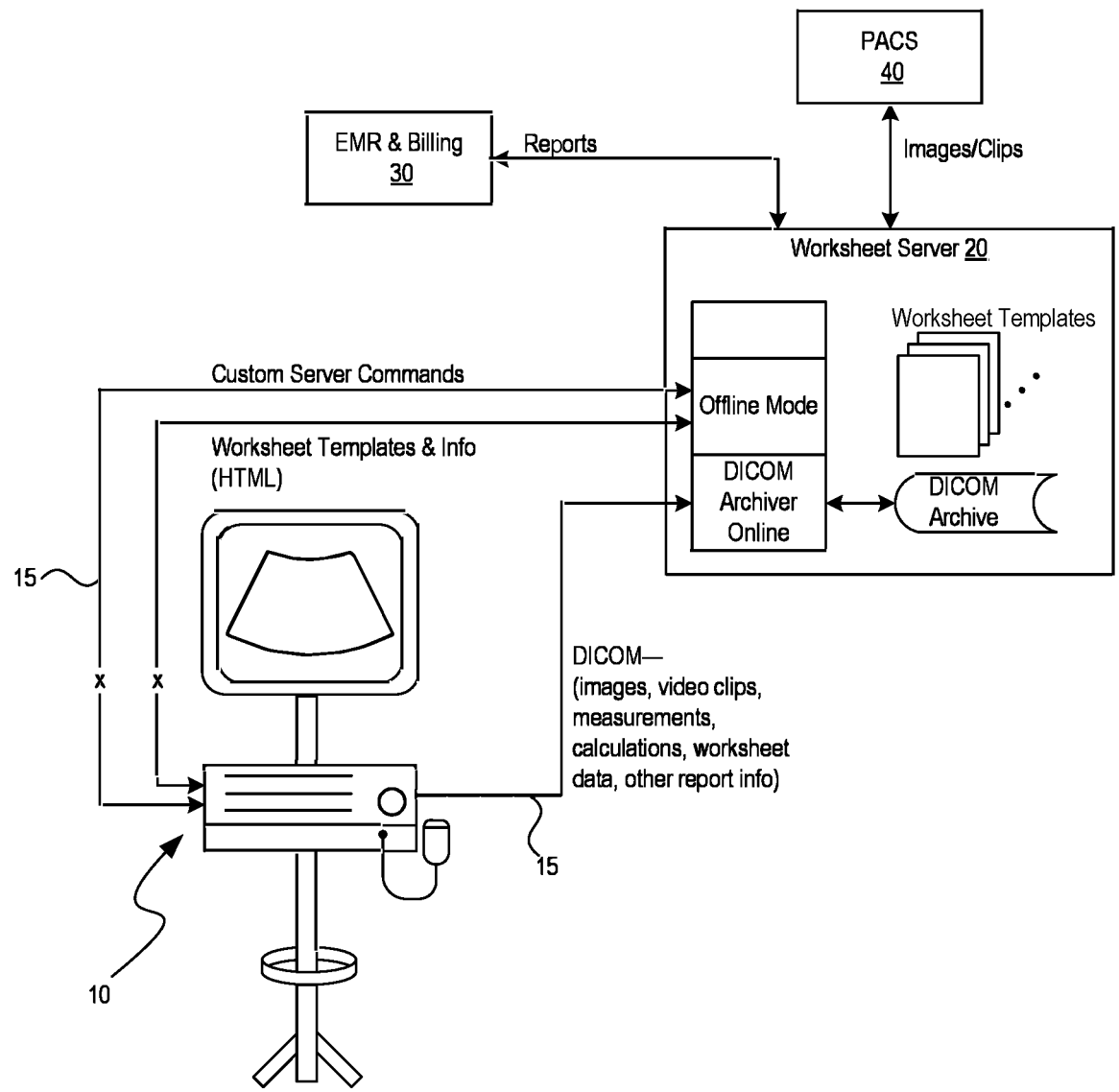
FIG. 1 shows a system for allowing a user to complete worksheets for an examination while being disconnected from a worksheet server in accordance with some embodiments of the disclosed technology.

The ability to utilize and complete worksheets in an offline setting improves point-of-care medical devices for providers who operate in the field or in settings were computer communication links are only periodic or suboptimal. For example, operators of ultrasound machines may examine patients in the field or in remote clinics that do not have computer communication links with sufficient bandwidth to allow a connection between an ultrasound machine and a remote worksheet server for the entire duration of an exam. Alternatively, medical imaging devices may be used at a patient's bedside without a cable or wireless connection to a computer communication link. Sometimes in an operating room or other emergency care situation, cabled network connections may be impractical, and wireless transmissions and connections in those environments may be limited by hospital policy interference requirements or the like. In existing systems, if a physician does not have access to a live network connection, the physician or an assistant takes notes during an exam that are later transcribed into a worksheet when a connection becomes available. Such a process slows workflow, requires additional effort, and introduces potential errors as the data is recorded and transferred into an electronic format.

To address these and other problems, the disclosed technology provides interaction on a point-of-care system with worksheets without a live connection to a remote worksheet server.

In many ultrasound point-of-care systems, and often in emergency medicine generally, it is the doctor who performs a scan and not a full time sonographer. Doctors who are not full-time sonographers are doing the scanning as part of the big picture care they are providing a patient in an emergency setting (unscheduled patients). Currently, there is no national or worldwide credentialing system for these physicians. Thus, each hospital must develop its own policy for determining that a doctor has the proficiency required to operate the device. One advantage of the technology disclosed herein is that a hospital can use it to record training hours, and QA/review in-training doctors' exams until they achieve their credentials in various applications. The disclosed technology aids in recording such examinations by allowing the physician to complete a worksheet after each examination.

Also, in emergency use cases, it is known that about 90% of the ultrasound scans do not get billed. In order to bill for services rendered, a medical service provider must be able to show that the attending physician is credentialed so that they can bill for the exam. The physicians are busy and do not have time to record the exam(s) from each modality, so that revenue does not get captured. The disclosed technology provides a way to automatically capture the answer to the question "what ultrasound exam(s) did you do on this patient that led to diagnosis and treatment?" and pass it on to the billing system. This information can be captured through completed worksheets so that a hospital or other service provider can charge for services rendered.

An organization can generate a custom set of worksheets, e.g., tailored for various departments, such as emergency medicine or radiology, and for the most common types of procedures performed. This facilitates use of such customized worksheets over default software embedded worksheets where a one size fits all approach is impractical and leads to infrequent or improper use.

The disclosed technology allows a physician to complete their worksheets as an examination is being performed without an active computer communication connection and without having to sign on to a remote server, such as a Qpath E server, at the end of the exam (or end of the day) and record their notes and "sign off" on the worksheet.

FIG. 1 is a block diagram of an ultrasound point-of-care system 10 in accordance with some embodiments of the disclosed technology. However, the disclosed technology can be used with other medical devices that implement worksheets (e.g. electrocardiogram machines, PET scanners, x-ray machines, etc.).

In the embodiment shown, the point-of-care system 10 is connected by a computer communication connection 15 to a worksheet server 20. The point-of-care system 10 includes one or more processors (not shown) that are configured to execute programmed instructions ("system software") that are stored in a computer readable memory in order to control the operation of the imaging system. The communication connection 15 to the worksheet server 20 may be a private wired or wireless LAN or may be a public network such as the internet. The worksheet server 20 stores a number of worksheets that can be customized for particular users, machines, groups of machines, or can be generic across an organization. Users can edit the worksheets, e.g. to put their own clinic logos on the forms or to make more substantive changes such as deciding what information or fields to include or not include and in what order, spaces for doctor or technician notes, and areas to put measurements or calculations.

The worksheet server 20 can store the data for a completed worksheet in a DICOM (Digital Imaging and Communications in Medicine) archiver. DICOM is a standard for handling, storing, printing, and transmitting information in medical imaging and records. It includes a file format definition and a network communications protocol. The information in a worksheet can be sent by the DICOM archiver to an electronic medical records (EMR) and billing system 30. In addition, images or video clips obtained during an examination can be stored on a picture archiving and communication (PACS) system 40. In some embodiments, when a patient record is pulled on the DICOM archiver, the worksheet server 20 pulls the referenced information back from the EMR system 30 and the PACS system 40.

When connected to the worksheet server 20, the ultrasound imaging system receives custom server commands as well as worksheets and other information over the computer communication connection 15. In various implementations, the worksheets can be obtained at various times, such as on a periodic basis, when the worksheet is loaded on the point-of-care system, upon an administrator command at the point-of-care system (i.e. a "pull" operation), or as a "push" from the worksheet server. Worksheets can be transmitted from the worksheet server 20 to the ultrasound imaging machine in a browser readable format such as HTML. In some implementations, worksheets can include JavaScript.

In some cases, worksheets can include references to other content such as images, scripts, CSS files, etc. These references can be network based or can be downloaded locally to the point-of-care system. For example, the worksheets and any referenced items can be downloaded and saved in local memory of the point-of-care system when a live network connection is available. The worksheet can then be used by the point-of-care system, whether or not a live network connection is available, because the worksheet and items referenced by the worksheet are available locally.

A browser component implemented by the system software running on the point-of-care system 10 can display the worksheets, allowing a user to enter data, attach images or video clips, and sign the worksheet electronically. Once the user has completed the worksheet, the entered data, images and video clips can be transmitted back to the worksheet server 20 for storage in the DICOM archive server once the computer communication connection is established.

In some implementations, when a user signs a worksheet within the browser component, the browser component can transmit the worksheet, e.g. by submitting a form encapsulating the worksheet. However, this option is not available if there is not a live network connection to a server. As indicated above, in a conventional system, the worksheets received from the worksheet server 20 are designed to operate in a browser environment that is continually connected to the worksheet server 20 through an active computer communication connection 15. If the communication link fails or is unavailable, any information entered into the worksheet and not yet saved may be lost. Additionally, switching between worksheets may cause an error or loss of data.

To allow operators of the point-of-care system to complete a worksheet when not connected to the worksheet server 20, the disclosed technology provides mechanisms by which system software running on the point-of-care system 10 can run functions (e.g. JavaScript functions) in relation to the HTML of a particular worksheet. Once retrieved, the system software can encapsulate the worksheet data in a DICOM package, e.g. as one or more private tags or in standard DICOM fields, and put the DICOM package into an outbound queue for transmission to a server upon a live network connection being available. In some implementations, whether or not there is a live network connection, the system software interfaces with the browser component to extract worksheet data. In other implementations, the browser component submits the worksheet data directly when a live network connection is available and interfaces with the system software when a live network connection is not available.

Figure 2:
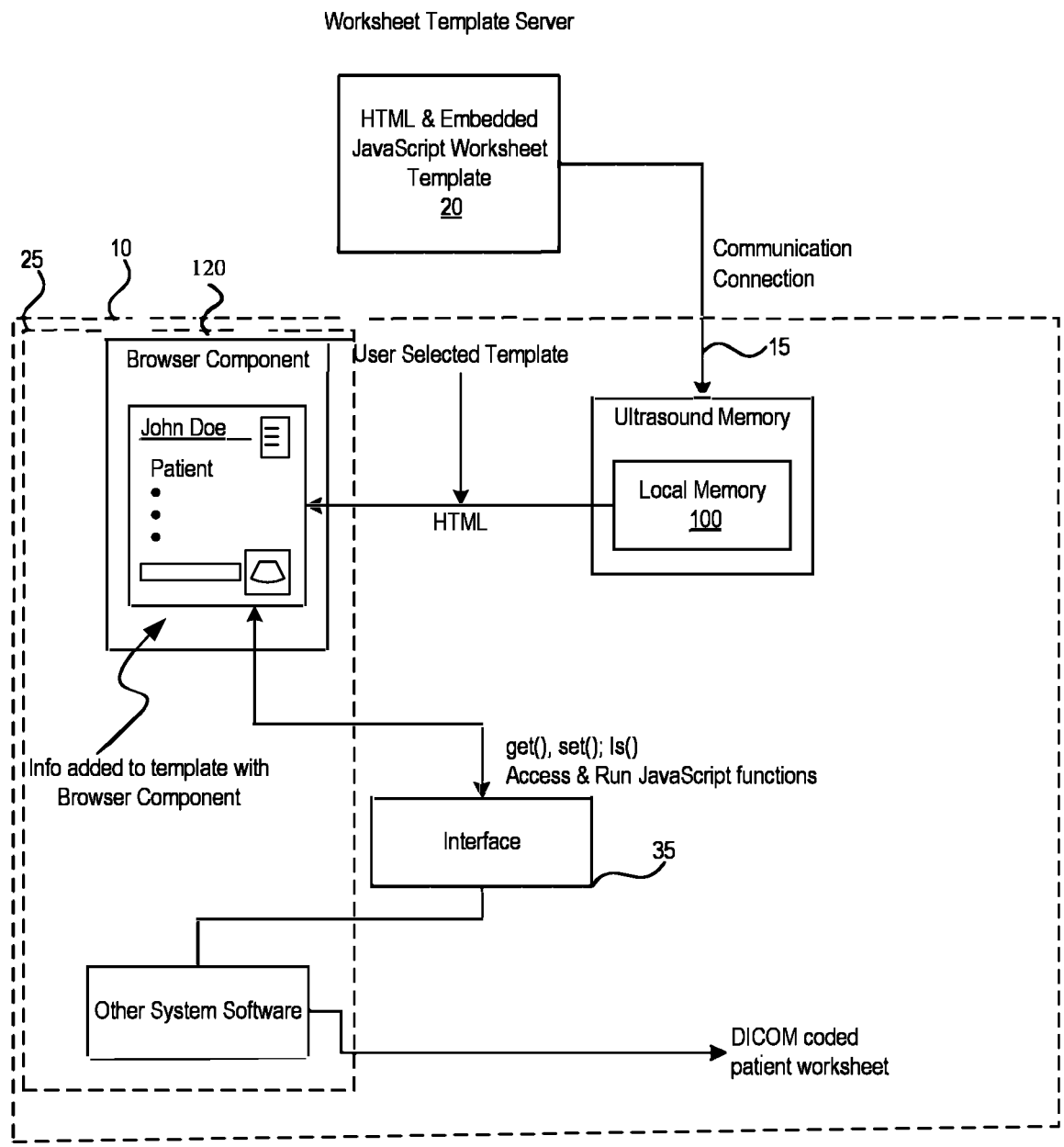
FIG. 2 is a block diagram of a system for accessing information included in a worksheet in accordance with some embodiments of the disclosed technology.

FIG. 2 is a block diagram of a system for allowing a user to complete a worksheet, previously downloaded from a remote worksheet server, without a live connection to the remote server. In the embodiment shown, worksheet server 20 connects to point-of-care system 10 using communication connection 15. A local memory 100 in the point-of-care system 10 stores the HTML and other files that define the one or more worksheets received from the worksheet server 20.

The system software 25 on the point-of-care system 10 includes a browser component 120 that allows a user to view and interact with the worksheets. With the browser component, the user can enter information, make and record measurements, and sign the worksheet. The browser component or system software can also be used to associate video clips, still images, or other information with the worksheet data.

As will be understood by those of skill in the art, the worksheets received from the worksheet server can include or reference a number of functions (e.g. JavaScript) that provide information about the worksheet that is rendered in the browser. For example, functions can produce drop-down menus, control radio buttons, display checkboxes and perform other operations that control how the worksheet appears. Some functions can provide meta-data about the worksheet, such as if the form contains any information, has been signed by the doctor or technician performing the examination, and the like. Such functions are generally designed to be within a browser component and do not communicate with outside applications, such as the other point-of-care system software. The technology disclosed provides ways for such external software to cause these functions to execute and to obtain their results.

In accordance with some embodiments of the disclosed technology, the system software 25 of the point-of-care system interfaces with the browser component to execute functions, either by using an intermediary component (e.g. interface 35) to obtain access to pre-defined functions included in, or referenced by the worksheets or by injecting functions into the script interpreter of the browser component. In some implementations, interface 35 can be a component object model (COM) interface provided by an operating system of the point-of-care system. In some embodiments the functions the interface can cause the browser to execute include:

GetWorksheetData( )—gets a form's user-entered data and any sign-off/approval credentials that are encapsulated a string-represented data object. This packaged data will be transferred to the worksheet server via DICOM encapsulation and private tags or by mapping the data to DICOM fields.

SetWorkSheetData(worksheetData)—sets the entire worksheet entered data including any sign-off/approval data according to worksheetData, which can be a string-represented data object (e.g. JSON) encapsulation.

IsWorksheetSigned( )—returns a Boolean value indicating if a worksheet has been signed.

IsWorksheetActive( )—returns a Boolean representing whether the worksheet has any user-entered data, saved or unsaved.

As will be appreciated, other functions that provide the information described above could also be used. The details of how such functions are written are considered to be known to those skilled in HTML and JavaScript. In implementations that use an intermediary component, the system software knows identification information for the functions, such as the function names, what types of variables are to be passed to the functions, what return values and their types are expected from the functions, code line number, memory location, identifier number, parent object, or other identifying information. The intermediary component can use this information to gain access to execute these functions and to obtain the functions' results. In other implementations, the access can be gained by the system software injecting the functions directly into the script interpreter of the browser component and, in response, receiving any produced results.

With this access, the system software can retrieve the information that a user has entered into the worksheet with the browser component and the meta-data about the worksheet itself. The system software stores the retrieved information in a local memory. This access also allows the system software to auto-fill the worksheet data back into a worksheet when it is re-opened. In addition, the system can take the information from a form and reconfigure the information as a DICOM file, either as entering pieces of the information into corresponding standard DICOM fields or into one or more private tags. A DICOM archive server can extract this information and worksheet identification information to determine that the information is for a particular worksheet. The system software sends the DICOM file when a live computer communication connection is established.

By allowing the system software to call these functions, the system software can retrieve the information that is entered into a worksheet and store it in local memory. The system software then can repackage the information into a DICOM file and transmit the information back to the DICOM archive server when a computer communication connection is re-established. In some embodiments, the system software stores the DICOM information for each worksheet periodically and as it is being closed. If a worksheet is opened again before the information is transmitted to the worksheet server 20, the system can invoke the JavaScript commands to restore the information into the worksheet in its previous state so that the physician or technician can finish the report.

In another embodiment, information about a worksheet that is being rendered by a browser component is obtained not by calling embedded scripts but via injecting additional scripting into the HTML DOM using supported functionality specific to some browser components, such as those used in WPF and UWP platforms.

Figure 3:
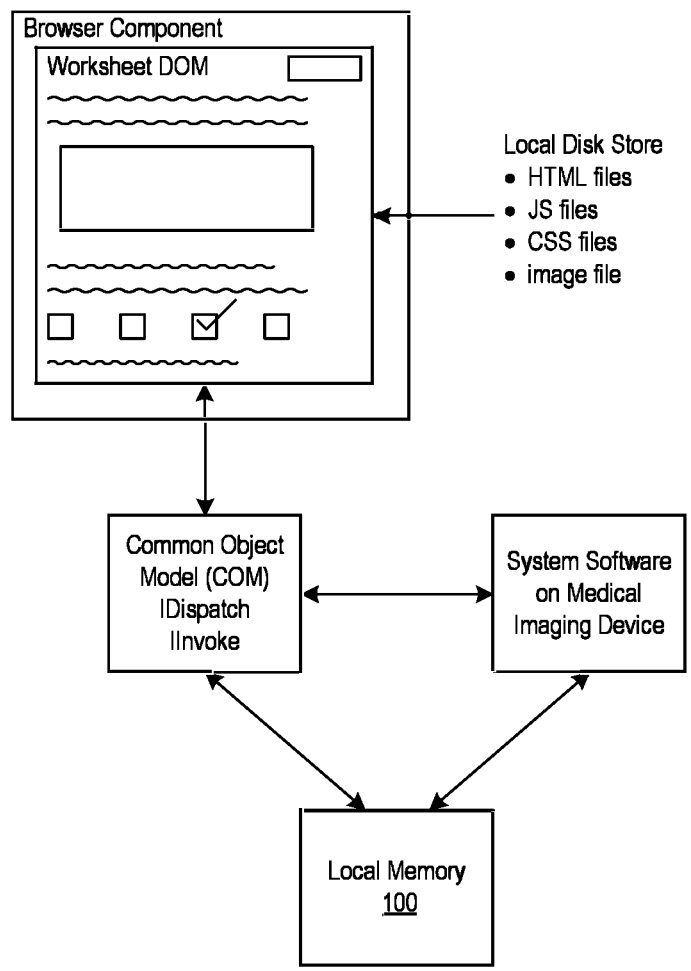
FIG. 3 is a block diagram of a system for interacting with embedded JavaScript functions by system software running on a medical imaging device in accordance with some embodiments of the disclosed technology.

FIG. 3 illustrates further detail of how the system software can interact with the browser component, using an intermediary component, to retrieve information about a worksheet in accordance with some embodiments of the disclosed technology. The information required to render a worksheet by a browser component is retrieved from the worksheet server 20 and stored in a local memory of the medical imaging device. The information that makes up a worksheet can include HTML text files, JavaScript files, cascading style sheet (CSS) files, or media (e.g. image, audio, video, etc.) files. These files can be stored in a directory (and subdirectories if required) of a local disk store on the medical imaging device. When a user selects a worksheet using a graphical user interface, the browser component loads the information for the worksheet and creates a document object model (DOM) corresponding to the worksheet.

In the example shown in FIG. 3, to access the information in the DOM for the rendered worksheet, the system software uses a component object model (COM) intermediary interface, which provides IDispatch and IInvoke commands. COM can use IDispatch to retrieve pointers to the pre-defined JavaScript functions that provide information about or auto-fill information into the worksheets. The system software can also configure arguments expected by the functions and define the expected results in manner that is understood by the COM interface. The system software then instructs the COM intermediary component to request execution of the functions, using the IInvoke command. Any results returned from the functions are placed into memory locations, in local memory 100, that are known to the system software.

Those skilled in the art will appreciate that the illustrated block diagram and flow diagram components may be altered in a variety of ways. For example, the order of the logic may be rearranged, substeps may be performed in parallel, illustrated logic may be omitted, other logic may be included, etc. In some implementations, one or more of the components described above can execute one or more of the processes described below.

Figure 4:
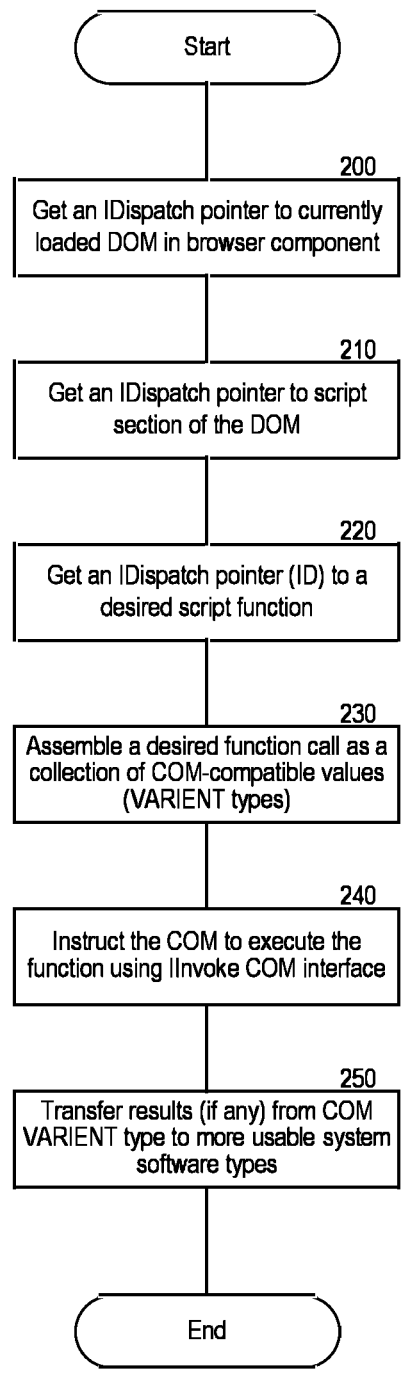
FIG. 4 is a flowchart of steps to interface between point-of-care system software and a browser component, using an intermediary component, to extract or auto-fill worksheet data in accordance with some embodiments of the disclosed technology.

FIG. 4 shows more detail of the actions performed by the system software to call the functions of the DOM corresponding to a worksheet in accordance with some embodiments of the disclosed technology. In some implementations, the process of FIG. 4 is implemented as a sub-process of block 610 or block 616 of the process shown in FIG. 6.

Beginning at 200, the system software calls the IDispatch function of the COM interface to obtain a pointer to the currently loaded DOM in the browser component. The pointer provides a handle to the worksheet that is currently being rendered. If the user is switching between worksheets, the pointers can be stored and the correct pointer for the currently rendered worksheet is used.

At 210, the system software calls the IDispatch function of the COM interface to get a pointer to a portion of the DOM that includes script functions. In some implementations, getting the pointer to the portion of the DOM that includes script functions can be based on the pointer to the currently loaded DOM. For example, the pointer to the currently loaded DOM can provide a scope or other context for the function that will obtain the pointer to the portion of the DOM that includes script functions. In some implementations, the scripts are JavaScript, however other script types can be used. For example, scripting and other languages such as VBScript, AJAX, jQuery, C#, Java, etc. could be used.

At 220, the system software calls the IDispatch function, passing identifications for one of the worksheet's functions, to retrieve a pointer to that function. As indicated above, the identifiers can include the names of these functions, which are known a priori to the system software. In some implementations, the system software requests the IDispatch function to return pointers to one or more of the JavaScript functions, for the current DOM in the browser component, having the names: "GetWorksheetData( )"; "SetWorkSheetData(worksheetData)"; "IsWorksheetSigned( )"; and "IsWorksheetActive( )". While the functions can have any name as long as the names are known to the system software, this naming convention is used here as examples because persons of ordinary skill in the art will understand what functions with these names are expected to do and would be able to create them. In some implementations, retrieving the pointers to the identified functions can be based on the pointer to the portion of the DOM that includes script functions. For example, the pointer to the portion of the DOM that includes script functions can provide a scope or other context for the function that will obtain the pointers to the identified functions.

The types of variables used and returned by these functions (e.g. in JavaScript) may not be the same as those used by the COM interface. Therefore, in the disclosed embodiments, the parameters passed to the function and returned from the function can be translated into types that are understood by the COM interface. At 230, the system software assembles a function call as a collection of COM compatible values (VARIANT types). In some embodiments, a function call is created as a structure. For example, a JavaScript function:

```
FunctionName (Arg1, Arg2, Arg 3 etc)
Could be encoded as the structure:
    COM:
        String name of the JavaScript function
        BSTR(FunctionName)
        List of parameters
        BSTR(string arguments)
            or VARIANT type
        VARIANT_Bool, VARIANT numerical units
```

At 240, the system software instructs the COM to execute the function using the IInvoke COM interface. For example to execute the GetWorksheetData( ) function, the COM interface is instructed to perform the following pseudocode:

```
{
    Create a COM VARIANT structure/union for the script function's return value, varResult.
    Create a COM BSTR representing the name of the script function to be executed, strFunc, set to "GetWorksheetData".
    create a COM BSTR representing an empty string for the script function's input parameter, param1, set to "".
    Create a COM IDispatch parameters structure/union for the arguments to the script function, dispparams.
    Add the single parameter, param1, to dispparams.
    if(no document pointer, pDisp){
        // A fresh document has been loaded into the browser component.
        Create a COM IDispatch pointer to the currently-loaded HTML document and save it in pDisp.
    }
    Using pDisp, get a COM IDispatch pointer to the script section of the HTML document, pScript.
    Using pScript, find the script function designated by strFunc, and create an IDispatch identifier for it, dispid.
    Using pScript and the COM Invoke, execute the script function, dispid, with arguments dispparams, and return value varResult.
    Wait for the script function to complete and for COM interface to copy the result into varResult.
    Since the expected return result of this script function is a string result, convert the BSTR part of varResult to a string (such as char*) usable by the system software.
}
```

At 250, the results (if any) of the called functions inside the current DOM are stored in the memory of the structure used to call the function and are converted from a format used by the COM interface into a format used by the system software. For example, BSTR used by the COM interface, containing data in JSON format, may be converted into a string character array, char[ ], char* that is used by the system software.

Figure 5:
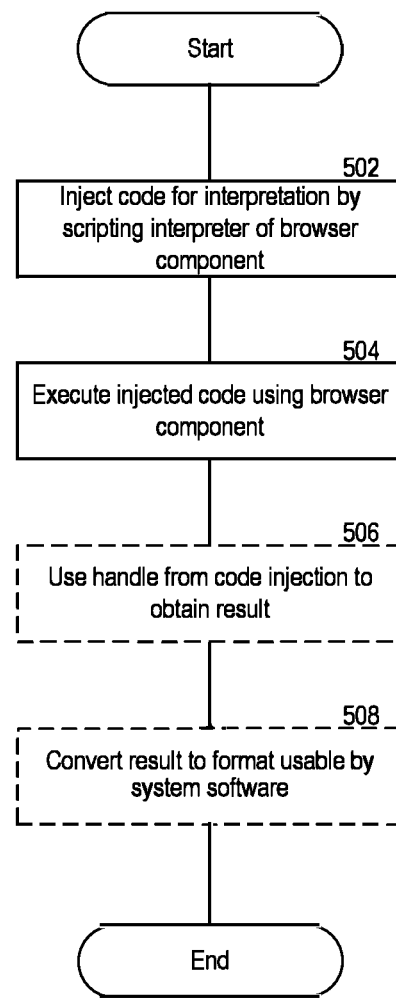
FIG. 5 is a flowchart of steps to interface between point-of-care system software and a browser component, using code injection, to extract or auto-fill worksheet data in accordance with some embodiments of the disclosed technology.

FIG. 5 shows more detail of the actions performed by the system software to inject functions into a browser component implementing a worksheet in accordance with some embodiments of the disclosed technology. In some embodiments, the process of FIG. 5 is implemented as a sub-process of block 610 or 616 of the process shown in FIG. 6.

At block 502, the system software of the point-of-care system can inject code (e.g. JavaScript) into the browser component for the browser component's scripting interpreter. In various implementations, injecting code into the browser can be performed using a call to an API provided by the browser component, by using a plug-in installed for the browser component and configured to receive scripts and inject them into a script section of a worksheet; by accessing the active DOM in the browser component and adding a script code to it, or by adding code through access points of the browser component, such as a URL bar. In each case, injecting code to the browser component can have one or more handles for obtaining results, if any, of the injected code. For example, a result handle can be a return value from an API or plug-in function call, a memory location shared between the browser component and the system software that the injected code is configured to write to, a call made by the injected code to a web service local to the point-of-care system, or the system software can be configured to intercept outgoing requests from the browser component and locally handle those with an identifier (e.g. a specified destination, port, etc.) indicating it is from the injected code.

At block 504, the browser component can execute the injected code. As discussed above, the injected code can include one or more functions comparable to the GetWorksheetData( ) SetWorkSheetData(worksheetData); IsWorksheetSigned( ) or IsWorksheetActive( ) functions discussed above.

In some implementations, blocks 506 and 508 can be performed only when the injected code is expected to produce a result, as indicated by these blocks being shown in dashed lines. At block 506, the system software can use a handle for the type of code injection used to obtain a result of the executed code.

In some implementations, the system software can receive a function call return value for an API or plug-in function call. In other implementations, the system software can read from a memory location shared between the browser component and the system software, to which the injected code is configured to write the result. In yet other implementations, the injected code can include an operation to make a network request (e.g. an operation in JavaScript using XMLHttpRequest( )) where the request destination can be a web service local to the point-of-care system and data encapsulated in the request (e.g. as GET or POST data) can be extracted by a script hosted by the local web service. Further, the system software can intercept outgoing requests from the browser component and extract the data encapsulated in the request.

At block 508, the result from the injected code can be converted into a format useable by the system software. For example, the result may be a string representation of the result, such as a JSON data string. In some implementations, the string can be tokenized and values with particular keys can utilized, e.g. by mapping them into corresponding DICOM fields. In other implementations, the entire string or values from the tokenized string can be encapsulated in a DICOM private tag.

Figure 6:
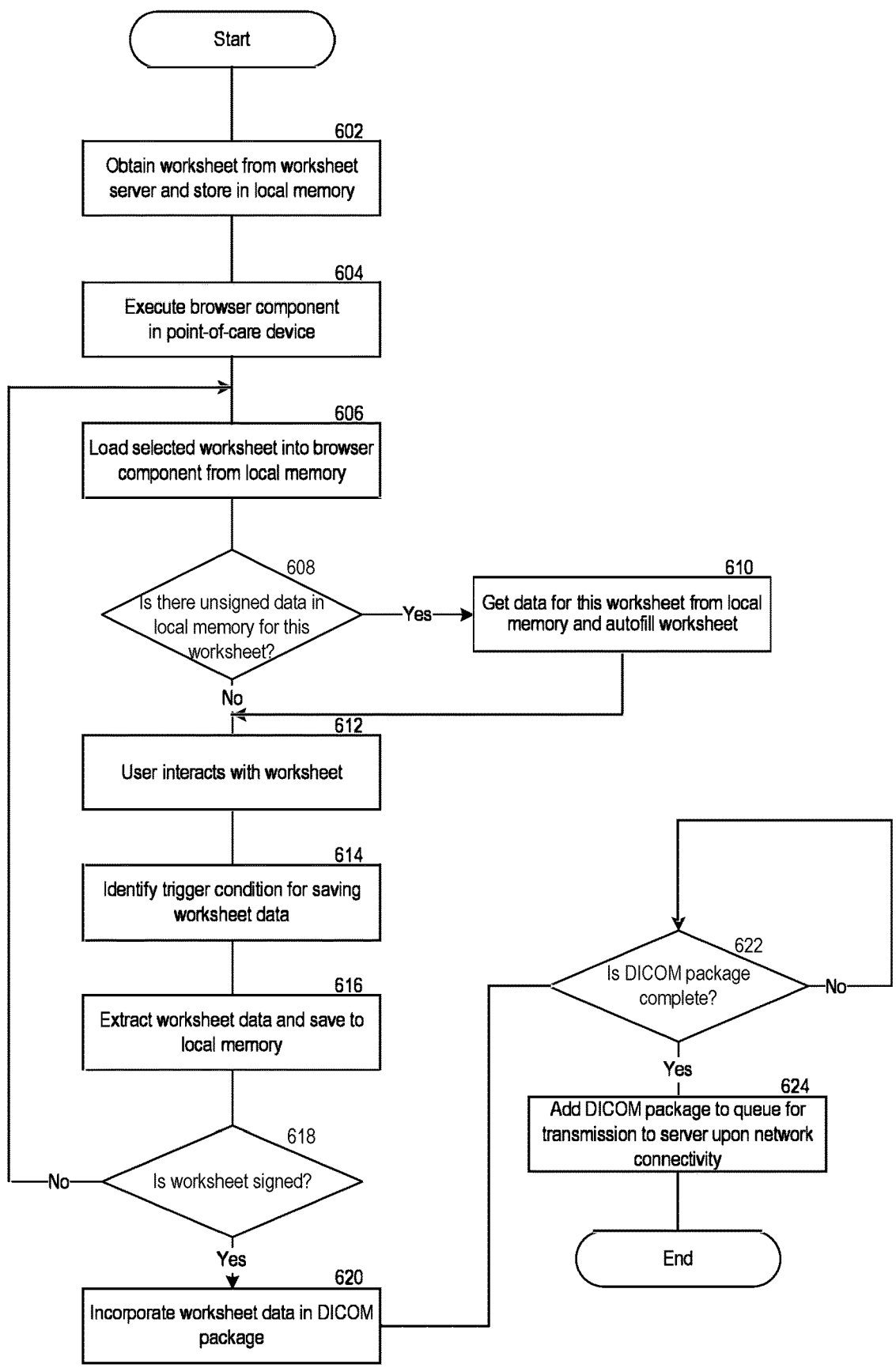
FIG. 6 is a flowchart of steps performed by system software to operate worksheets, using local storage instead of a live server connection, and to transmit worksheet data upon server availability in accordance with some embodiments of the disclosed technology.

FIG. 6 is a flowchart of steps performed by system software to operate worksheets, using local storage instead of a live server connection, and transmit worksheet data upon server availability in accordance with some embodiments of the disclosed technology. At block 602, the system software can obtain worksheets, from a worksheet server, and store them in local memory. In various implementations, obtaining versions of worksheets can be initiated by a requesting device (i.e. a "pull" operation) or by the worksheet server (i.e. a "push" operation). In various implementations, obtaining versions of worksheets can be triggered by an administrator command (either locally or from a remote system), by a periodic automatic request for updates, when a new version of a worksheet is available, or in response to a user requesting to access a worksheet while there is an active connection to a worksheet server.

By using worksheets from a worksheet server, the worksheets can be customized for particular organizations, e.g. to maintain a particular look and feel, to include particular fields corresponding to data an organization wants to gather at that point-of-care system, or to specify how fields in the worksheet are organized to enable particular data-gathering workflows. The worksheets can be customized for a particular point-of-care system or for a group of point-of-care systems. In some implementations, the worksheets can be files that define fields using HTML. In some implementations, the worksheet files can include other content, such as scripts (e.g. JavaScript), images or other media, CSS, etc. Alternatively or in addition, the worksheet files can include references to other content stored in local storage of the point-of-care system. This allows the other content to be shared among worksheets and allows worksheets to be updated without having to re-download portions of the worksheet that haven't changed. In some implementations, the worksheets and/or the additional content can be stored in a solid state drive of the point-of-care system. In some implementations, the worksheets and/or the additional content can be stored in a secure manner, such as through encryption.

Once block 602 is complete, the worksheets and their corresponding other content has been stored locally. In addition and as discussed below, the point-of-care system is able to extract and locally store data entered into a worksheet. As a result, once block 602 is complete, the point-of-care system can implement remaining blocks 604-624 without a live server connection.

At block 604, the system software of the point-of-care system can execute a browser component. This can be a custom browser specific to the point-of-care system or a version of a commercial browser, such as Chrome, Safari, Internet Explorer, etc. In some implementations, the browser component can be configured to integrate with, or be embedded in the system software such that it is not readily apparent that the browser component is separate from other aspects of the system software. In various implementations, executing the browser component can be performed as part of the initialization of the system software or in response to a user selection to open a worksheet.

At block 606, the browser component can load, from local memory, a selected worksheet, e.g. selected by a user during a patient exam. This can be accomplished by supplying the worksheet, from where it was stored in local memory at block 602, to the browser component. Where the worksheet has references to other content stored in local memory, the browser component can resolve the references and obtain the other content to fully render the worksheet and execute additional code such as referenced JavaScript or CSS.

At block 608, the system can determine whether there is unsigned or otherwise partial data stored in the local memory for the worksheet loaded at block 606. In some implementations, this occurs by checking which worksheet was loaded at block 606 and determining whether corresponding worksheet data has been stored. For example, meta-data identifying a worksheet can be stored in association with the worksheet data in the local memory. Worksheet data can be recognized where it has not yet been signed-off for transmission to a DICOM server, which can be indicated by further meta-data. In some implementations, the point-of-care system can include session data identifying a current patient, in which case at block 608 the determination further identifies unsigned worksheet data only if it also has an identifier for the current patient. If worksheet data is identified at block 608, processing continues to block 610. Otherwise, processing continues to block 612.

At block 610, the worksheet data identified at block 608 can be obtained from the local storage and supplied to the browser component. Code included in the worksheet or injected by the system software can use the supplied worksheet data to auto-fill fields of the worksheet. A process for inserting worksheet data into worksheet fields using an intermediary component is described above in relation to FIG. 4. A process for inserting worksheet data into the worksheet using code injection is described above in relation to FIG. 5.

At block 612, a user and/or automated systems can interact with the worksheet. For example, a user can type information into a field or other gathered data can be entered or associated with the worksheet, such as data scanned from an encoding (e.g. a bar-code, QR code, etc.), calculations, measurements, images, readings, other scanning results, etc.

At block 614, a trigger condition for saving the worksheet data can be identified. In some implementations, the trigger condition can be an event that will cause the browser component to navigate away from the current page, which can result in the browser component clearing the DOM for the current worksheet. For example, such events can include a user actuating a control to end a patient exam, navigating to a different worksheet or other page, or an activation of a different sub-system of the point-of-care system (e.g. imaging, transducer, system menu, help menu, etc.) which will cause the system software to close the browser component.

At block 616, data entered into the current worksheet can be extracted and saved to local memory. Extracting data from the worksheet, for example, can be accomplished by utilizing an intermediary component to identify a reference to a GetWorksheetData( ) function and execute the function or by injecting the code for a GetWorksheetData( ) function into the browser component and retrieving the result. A process for extracting data from the worksheet using an intermediary component is described above in relation to FIG. 4. A process for extracting data from the worksheet using code injection is described above in relation to FIG. 5. The extracted worksheet data can be saved in a secure manner, such as by being encrypted.

At block 618, the system software can determine whether the worksheet data has been signed. In various implementations, this can be accomplished by examining a variable embedded in or otherwise associated with the extracted worksheet data (e.g. meta-data) or by using the intermediary component or code insertion to execute an IsWorksheetSigned( )function. If the worksheet has not been signed, processing returns to block 606 when a worksheet is again selected to be loaded in the browser component. If the worksheet has been signed, processing continues to block 620.

At block 620, the system software can incorporate a version of the signed worksheet data into a DICOM package. In some implementations, this is done by adding a version of the worksheet data, e.g. as a string, to a private tag in the DICOM package. When a server receives this DICOM package it can extract individual values from the worksheet data in the private tag. In other implementations, the version of the worksheet data can be values for individual fields of the worksheet extracted from the worksheet data and added to corresponding standard fields of a DICOM package.

At block 622, the system software can determine whether the DICOM package is complete. In some implementations, the system software can determine a DICOM package is complete when a specified set of materials is included, such as images, reports, worksheet data, other meta-data, etc. In other implementations, the system software identifies a DICOM package as complete when a user provides an indication to this effect, such as by clicking on an end exam control. If the DICOM package is not complete, processing remains at block 622 until additional input is received indicating the DICOM package is complete. Once the DICOM package is complete, processing continues to block 624.

At block 624, the system software can add the completed DICOM package to a queue configured to transmit DICOM packages in the queue to one or more servers when live network connectivity is available.

Figure 7:
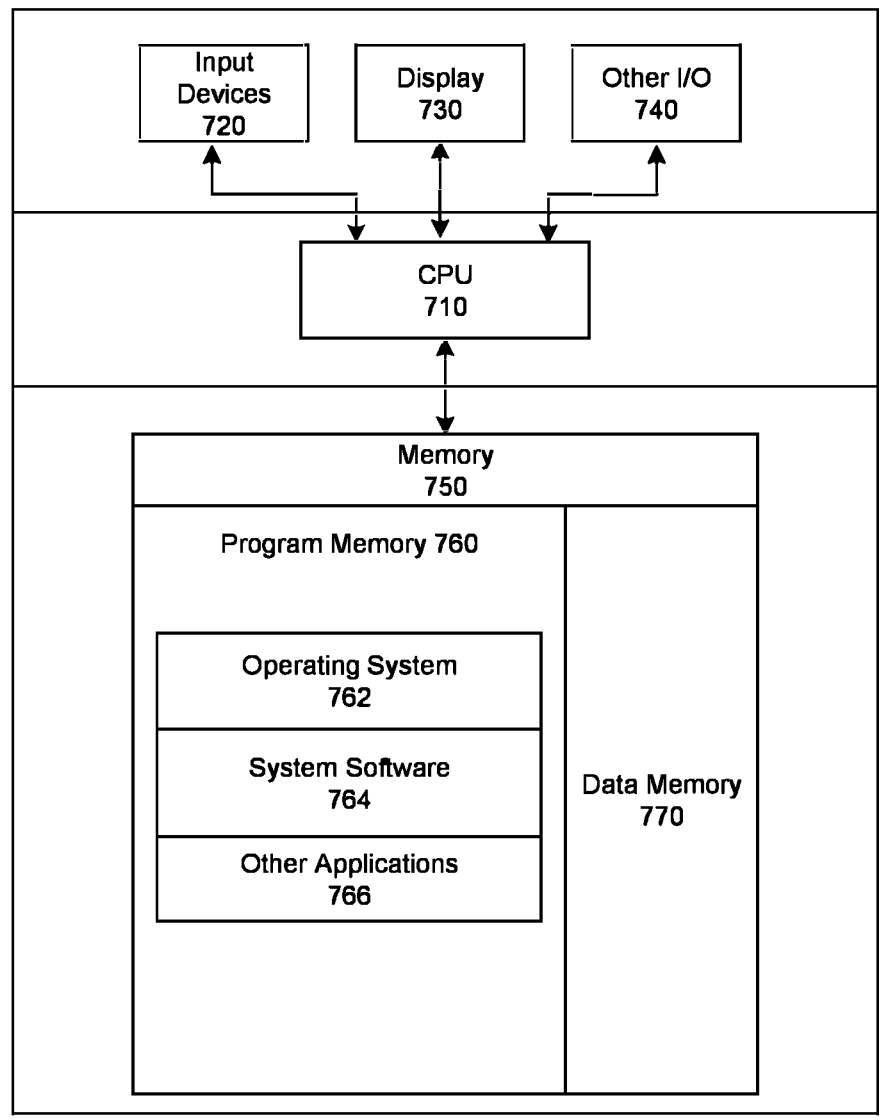
FIG. 7 is a block diagram of an example computing component for executing system software on a point-of-care medical imaging system in accordance with some embodiments of the disclosed technology.

FIG. 7 is a block diagram of an example computing component 700 for executing system software on a point-of-care medical imaging system in accordance with some embodiments of the disclosed technology. Elements of computing component 700 can be implemented in digital electronic circuitry, or in computer software, firmware, or hardware, including the structures disclosed in this specification and their structural equivalents, or in combinations of one or more of them. Computing component 700 can include one or more input devices 720 that provide input to the Processor(s) 710 (e.g. CPU(s), GPU(s), HPU(s), etc.), notifying it of actions. The actions can be mediated by a hardware controller that interprets the signals received from the input device and communicates the information to the processors 710 using a communication protocol. Input devices 720 include, for example, a mouse, a keyboard, a touchscreen, an ultrasound, x-ray or other medical scanning component, an infrared sensor, a touchpad, a wearable input device, a camera- or other visual-based input device (e.g. bar-code or QR code reader), a microphone, or other user input devices.

Processors 710 can be a single processing unit or multiple processing units in a device or distributed across multiple devices. Processors suitable for the execution of a computer program include, by way of example, both general and special purpose microprocessors, and any one or more processors of any kind of digital computer. Processors 710 can be coupled to other hardware devices, for example, with the use of a bus, such as a PCI bus or SCSI bus. The processors 710 can communicate with a hardware controller for devices, such as for a display 730. Display 730 can be used to display text and graphics. In some implementations, display 730 provides graphical and textual visual feedback to a user. In some implementations, display 730 includes the input device as part of the display, such as when the input device is a touchscreen or is equipped with an eye direction monitoring system. In some implementations, the display is separate from the input device. Examples of display devices are: an LCD display screen, an LED display screen, a projected, holographic, or augmented reality display (such as a heads-up display device or a head-mounted device), and so on. Other I/O devices 740 can also be coupled to the processor, such as a network card, video card, audio card, USB, camera, printer, speakers, CD-ROM drive, DVD drive, disk drive, or Blu-Ray device.

In some implementations, the computing component 700 also includes a communication device capable of communicating wirelessly or wire-based with a network node. The communication device can communicate with another device or a server through a network using, for example, TCP/IP protocols. Computing component 700 can utilize the communication device to distribute operations across multiple network devices.

The processors 710 can have access to a memory 750 of the point-of-care system. A memory includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. Memory 150 can include program memory 760 that stores computer programs, such as an operating system 762 (e.g. Windows, AppleOS, Unix, etc.), system software (with a browser component) 764, and other application programs 766. Memory 750 can also include data memory 770 that can store data, such as worksheets and worksheet data, to be provided to the program memory 760 or any element of the computing component 700.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

Several implementations of the disclosed technology are described above in reference to the figures. Reference in this specification to "embodiments" or "implementations" (e.g. "some implementations," "various implementations," "one implementation," "an implementation," etc.), and the like, means that a particular feature, structure, or characteristic described in connection with the implementation is included in at least one implementation of the disclosure. The appearances of these phrases in various places in the specification are not necessarily all referring to the same implementation, nor are separate or alternative implementations mutually exclusive of other implementations. Moreover, various features are described which may be exhibited by some implementations and not by others. Similarly, various requirements are described which may be requirements for some implementations but not for other implementations.

Relative terms, such as high or unimportant, when not otherwise defined, can be understood as assigning a value and determining how that value compares to an established threshold. For example, the phrase "selecting a fast connection" can be understood to mean selecting a connection that has a value assigned corresponding to its connection speed that is above a threshold. As used herein, the word "or" refers to any possible permutation of a set of items. For example, the phrase "A, B, or C" refers to at least one of A, B, C, or any combination thereof, such as any of: A; B; C; A and B; A and C; B and C; A, B, and C; or multiple of any item such as A and A; B, B, and C; A, A, B, C, and C; etc.

Although the subject matter has been described in language specific to structural features and/or methodological acts, it is to be understood that the subject matter defined in the appended claims is not necessarily limited to the specific features or acts described above. Specific embodiments and implementations have been described herein for purposes of illustration, but various modifications can be made without deviating from the scope of the embodiments and implementations. The specific features and acts described above are disclosed as example forms of implementing the claims that follow. Accordingly, the embodiments and implementations are not limited except as by the appended claims.

Any patents, patent applications, and other references noted above are incorporated herein by reference. Aspects can be modified, if necessary, to employ the systems, functions, and concepts of the various references described above to provide yet further implementations. If statements or subject matter in a document incorporated by reference conflicts with statements or subject matter of this application, then this application shall control.

The invention claimed is:

1. A medical device comprising:
   a local memory;
   a browser component coupled to the local memory;
   a system component separate from the browser component; and
   one or more processors coupled to the local memory, the browser component and the system component, wherein the one or more processors are configured to:
      determine that the medical device does not have a live connection to the server;
      obtain one or more worksheets from a server and store the one or more worksheets in the local memory;
      load a worksheet from the one or more worksheets in the local memory into the browser component;
      obtain, via the system component, a first reference to a first function associated with the worksheet loaded into the browser component;
      execute, based on the first reference, the first function to extract, via the system component, worksheet data from the worksheet;
      store the worksheet data in a portion of the local memory inaccessible to the browser component; and
      transfer the worksheet data from the portion of the local memory to a queue, wherein loading the worksheet, obtaining the first reference, executing the first function, storing the worksheet data, and transferring the worksheet data are responsive to determining that the medical device does not have the live connection to the server;
      determine that the live connection to the server is available; and
      transmit the worksheet data, from the queue, to the server in response to determining that the live connection to the server is available, wherein the worksheet includes HTML content and one or more references to one or more pieces of additional content stored in the local memory, the one or more pieces of additional content comprising a script stored in the local memory; and
   wherein the loading the worksheet comprises:

resolving the one or more references by retrieving the additional content from the local memory and compiling the HTML content and the additional content into a document object model ("DOM").

2. The medical device of claim 1, wherein the one or more processors are further configured to:
obtain, via the system component, a second reference to a second function associated with the worksheet; and
execute the second function to auto-fill, via the system component, the worksheet data into the worksheet based on the second reference.

3. The medical device of claim 1, wherein the first function is a script function.

4. The medical device of claim 1, wherein the system component is a component object model, and wherein the one or more processors are configured to:
execute a first command of the component object model that uses at least a name of the first function to obtain a pointer to the first reference to obtain the first reference to the first function; and
execute a second command of the component object model that uses the pointer to the first function and arguments defined for the component object model to cause the browser component to execute the first function.

5. The medical device of claim 1, wherein the one or more processors are configured to:
identify a trigger condition that causes the browser component to navigate away from the worksheet; and
extract, via the system component, the worksheet data from the worksheet in response to identifying the trigger condition.

6. The medical device of claim 1, wherein at least a portion of the worksheet data is at least one of a string or data entered into digital imaging and communication in medicine ("DICOM") tags.

7. The medical device of claim 1, wherein the one or more processors are further configured to:
inject code into the browser component that causes the browser component to execute the injected code; and
receive, in response to the code injection, a result that includes the worksheet data.

8. The medical device of claim 1, wherein the one or more processors are further configured to:
determine the worksheet data stored in the local memory based on worksheet meta-data;
obtain the worksheet data from the local memory, and
auto-fill, via the system component, at least a portion of the worksheet data into the worksheet.

9. The medical device of claim 1, wherein the one or more processors are further configured to:
determine, based on worksheet meta-data, that the worksheet data has been signed; and
incorporate at least a portion of the worksheet data in a private tag of a DICOM package.

10. A method for operating a medical device comprising a local memory, and one or more processors coupled to the local memory that are configured to execute a system software that includes a browser component and a system component that is separate from the browser component, the method comprising:
determining that the medical device does not have a live connection to the server;
obtaining, by the one or more processors, one or more worksheets from a server and store the one or more worksheets in the local memory;
loading a worksheet from the one or more worksheets in the local memory into the browser component;
obtaining, via the system component, a first reference to a first function associated with the worksheet loaded into the browser component;
executing, based on the first reference, the first function to extract, via the system component, the worksheet data from the worksheet;
storing the worksheet data in a portion of the local memory inaccessible to the browser component; and
transferring the worksheet data from the portion of the local memory to a queue, wherein loading the worksheet, obtaining the first reference, executing the first function, storing the worksheet data, and transferring the worksheet data are responsive to determining that the medical device does not have the live connection to the server;
determining that the live connection to the server is available;
and
transmitting the worksheet data, from the queue, to the server in response to determining that the live connection to the server is available, wherein the worksheet includes HTML content and one or more references to one or more pieces of additional content stored in the local memory, the one or more pieces of additional content comprising a script stored in the local memory; and
wherein the loading the worksheet comprises:
resolving the one or more references by retrieving the additional content from the local memory and compiling the HTML content and the additional content into a document object model ("DOM").

11. The method of claim 10, wherein the operations further comprise:
obtaining, via the system component, a second reference to a second function associated with the worksheet; and
executing the second function to auto-fill, via the system component, the worksheet data into the worksheet based on the second reference.

12. The method of claim 10, wherein at least a portion of the worksheet data is at least one of a string or data entered into digital imaging and communication in medicine ("DICOM") tags.

13. The method of claim 10, wherein the system component is a component object model, and wherein the operations further comprise:
executing a first command of the component object model that uses at least a name of the first function to obtain a pointer to the first function to obtain the first reference to the first function; and
executing a second command of the component object model that uses the pointer to the first function and arguments structured for the component object model to cause the browser component to execute the first function.

14. The method of claim 10, wherein the extract the worksheet data comprises:
injecting code into the browser component that causes the browser component to execute the injected code; and
receiving, in response to the code injection, a result that includes the worksheet data.

15. The method of claim 10, wherein the operations further comprise:
determining the worksheet data stored in the local memory based on worksheet meta-data;
obtaining the worksheet data from the local memory, and auto-filling, via the system component, at least a portion of the worksheet data into the worksheet.

16. The method of claim 10, wherein the operations further comprise:
   determining, based on worksheet meta-data, that the worksheet data has been signed; and
   incorporating at least a portion of the worksheet data in a private tag of a DICOM package.

17. The method of claim 10, wherein the operations further comprise:
   identifying a trigger condition that causes the browser component to navigate away from the worksheet; and
   extracting, via the system component, the worksheet data from the worksheet in response to identifying the trigger condition.

18. A non-transitory computer-readable storage medium storing instructions that, when executed by a computing system, cause the computing system to perform a method for operating a medical device that comprises a local memory, and one or more processors coupled to the local memory, wherein the one or more processors are configured to execute a system software that includes a browser component and a system component that is separate from the browser component, the method comprising:
   determining that the medical device does not have a live connection to the server;
   obtaining one or more worksheets from a server and store the one or more worksheets in the local memory;
   loading a worksheet from the one or more worksheets in the local memory into the browser component;
   obtaining, via the system component, a first reference to a first function associated with the worksheet loaded into the browser component;
   extracting, via the system component, the worksheet data, from the worksheet, by executing, based on the first reference, the first function;
   storing the worksheet data in a portion of the local memory inaccessible to the browser component; and
   transferring the worksheet data from the portion of the local memory to a queue, wherein loading the worksheet, obtaining the first reference, executing the first function, storing the worksheet data, and transferring the worksheet data are responsive to determining that the medical device does not have the live connection to the server;
   determining that the live connection to the server is available; and
   transmitting the worksheet data, from the queue, to the server in response to determining that the live connection to the server is available, wherein the worksheet includes HTML content and one or more references to one or more pieces of additional content stored in the local memory, the one or more pieces of additional content comprising a script stored in the local memory; and
wherein the loading the worksheet comprises:
   resolving the one or more references by retrieving the additional content from the local memory and compiling the HTML content and the additional content into a document object model ("DOM").

* * * * *